US009603875B1

(12) United States Patent
Glenn et al.

(10) Patent No.: US 9,603,875 B1
(45) Date of Patent: Mar. 28, 2017

(54) **METHOD OF MAKING A CONSUMABLE PRODUCT WITH PURIFIED EMBRYONATED *TRICHURIS SUIS* OVA**

(71) Applicant: NeuOva, LLC, Wilmington, NC (US)

(72) Inventors: Stephan D. Glenn, Weston, FL (US); Daniel T. Gregory, Jr., Hampstead, NC (US); Roy A. Stimits, Wilmington, NC (US); Frank Detlev Goj, Hamburg (DE)

(73) Assignee: NeuOva, LLC, Wilmington, NC (US)

( * ) Notice: Subject to any disclaimer, the term of this patent is extended or adjusted under 35 U.S.C. 154(b) by 0 days.

(21) Appl. No.: 14/990,074

(22) Filed: Jan. 7, 2016

(51) Int. Cl.
| | | |
|---|---|---|
| *A61K 39/02* | (2006.01) | |
| *A61K 35/62* | (2006.01) | |
| *A23L 1/30* | (2006.01) | |
| *A23K 1/16* | (2006.01) | |

(52) U.S. Cl.
CPC ............... *A61K 35/62* (2013.01); *A23K 1/16* (2013.01); *A23L 1/30* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,764,838 B2 | 7/2004 | Weinstock et al. | |
| 7,250,173 B2 | 7/2007 | Weinstock et al. | |
| 7,771,923 B2 | 8/2010 | Abromeit | |
| 7,833,537 B2 | 11/2010 | Weinstock et al. | |
| 8,993,332 B2 | 3/2015 | Tewes et al. | |
| 9,017,700 B2 * | 4/2015 | Wilhelm .................. | A01N 1/02 422/12 |
| 9,095,595 B2 | 8/2015 | Kapel et al. | |
| 2003/0039666 A1 | 2/2003 | Weinstock et al. | |
| 2004/0202671 A1 | 10/2004 | Weinstock et al. | |
| 2005/0118655 A1 | 6/2005 | Weinstock et al. | |
| 2006/0024333 A1 | 2/2006 | O'Connor | |
| 2007/0076868 A1 * | 4/2007 | Ming | |
| 2007/0298011 A1 | 12/2007 | Weinstock et al. | |
| 2008/0119534 A1 * | 5/2008 | Mjalli | |
| 2010/0260861 A1 | 10/2010 | Weinstock et al. | |
| 2010/0303721 A1 | 12/2010 | Weinstock et al. | |
| 2015/0087616 A1 | 3/2015 | Ritter et al. | |
| 2015/0174178 A1 | 6/2015 | Kovarik et al. | |
| 2015/0216932 A1 | 8/2015 | Hartmann et al. | |
| 2015/0306144 A1 | 10/2015 | Borody | |
| 2015/0306155 A1 | 10/2015 | Borody | |
| 2015/0306156 A1 | 10/2015 | Borody | |

FOREIGN PATENT DOCUMENTS

WO WO2014121020 A2 8/2014

OTHER PUBLICATIONS

Jouvin, M.H. and Kinet, JP., Trichuris suis ova: testing a helminth-based therapy as an extension of the hygiene hypothesis. J. Allergy Clin. Immunol. (2012) 130(1):3-10; quiz 11-2. doi: 10.1016/j.jaci.2012.05.028.
Summers, R.W., Elliott, D.E., Urban, J.F. Jr., et al., Trichuris suis therapy for active ulcerative colitis: a randomized controlled trial. American Gastroenterological Association 0016-5085/05, DOI:10.1053/ j.gastro.2005.01.005 (2005a) 128(4):825-32, USA.
Summers, R.W., Elliott, D.E., Urban, J.F. Jr., et al, Trichuris suis therapy in Crohn's disease. (2005b) Gut. 54:87-90. doi: 10.1136/gut.2004.041749, USA.
Fleming, J.O., Isaak, A, Lee, J.E., et al., Probiotic helminth administration in relapsing—remitting multiple sclerosis: a phase 1 study. NIH, Mult Scler. Jun. 2011; 17(6): 743-754. DOI:10.1177/1352458511398054, United States.
Ebner F, Hepworth MR, Rausch S., et al., Therapeutic potential of larval excretory/secretory proteins of the pig whipworm Trichuris suis in allergic disease. John Wiley & Sons A/S. Allergy (2014) 69: 1489-1497, USA.
Brannen, J.P., Garst, D.M., and Langley, S., Inactivation of Ascaris Lumbricoides Eggs by Heat, Radiation, and Thermoradiation. Issue 163 of SAND (Series) (Albuquerque, NM). (1975) 26 pages. Publisher: Sandia National Laboratories for the U.S. Department of Energy, available from the National Technical Information Service, Springfield, VA.
Nelson, K.L. and Darby, J.L., Inactivation of Viable Ascaris Eggs by Reagents during Enumeration. Appl. Environ. Microbiol (2001) 67(12): 5453-5459. doi: 10.1128/AEM.67.12.5453-5459.
Henson, M. and Burkes, A.W., The future of food allergies therapeutics. Semin Immunopathol (2012) 34 (5):703-14.
Vejzagic, N., Thamsborg, S.M., Kringel, H., et al., In vitro hatching of Trichuris suis eggs. Parasitol Res. Jul. 2015; 114(7):2705-14. DOI 10.1007/s00436-015-4476-1. Epub May 27, 2015.
Vejzagic, N., Adelfio, R., Keiser, J., et al., Bacteria-induced egg hatching differs for Trichuris muris and Trichuris suis. Parasites & Vectors. (2015b) 8:371.
Nacapunchai, D., Lamom, C., Boonsongpairod, B. et al., Factors affecting the hatching of human pinworm ova. Southeast Asian J Trop Med Public Health. (2002) 33 Suppl 3:76-8.

* cited by examiner

*Primary Examiner* — Jennifer Graser
(74) *Attorney, Agent, or Firm* — Louis Ventre, Jr.

(57) ABSTRACT

A method of making a consumable product containing purified embryonated *Trichuris suis* ova (TSO) preferably includes steps of: storing the TSO in an acidic solution; adding a food preservative to the acidic solution to produce a preservative-acid-solution; forming a mixing solution by raising the pH of the preservative-acidic-solution to match the pH of a food substance by titrating the preservative-acidic-solution with an acid neutralizer so that the pH changes at a rate of not more than 1 pH unit per 24 hours, preferably to a pH not higher than 5.0; and producing the consumable product by combining the mixing solution and the food substance while maintaining the temperature of the consumable product between 1 degree Centigrade and 47 degrees Centigrade.

13 Claims, 2 Drawing Sheets

Method of making: A method of making a consumable product, the consumable product comprising a purified embryonated Trichuris suis ova
100

Storing step: storing a purified embryonated Trichuris suis ova in an acidic solution
105

First-adding step: adding a food preservative to the acidic solution to produce a preservative-acid-solution
110

First-forming step: forming a mixing solution by raising the pH of the preservative-acidic-solution to match the pH of a food substance by titrating the preservative-acidic-solution with an acid neutralizer so that the pH changes at a rate of not more than 1 pH unit per 24 hours
115

Producing-step: producing the consumable product by combining the mixing solution and the food substance, said producing performed while maintaining the temperature of the consumable product between 1 degree Centigrade and 47 degrees Centigrade
120

FIG.1

| Making step: making the acidic solution using a formulation selected from the group consisting of vinegar, phosphoric acid, acetic acid, and citric acid 205 |
|---|
| First-selecting step: selecting the food preservative from at least one of sodium citrate, sodium sorbate, and sodium benzoate 210 |
| First-limiting step: limiting the sodium sorbate to a concentration of less than 0.3% sorbate in the acid solution 215 |
| Second-limiting step: limiting the sodium benzoate to a concentration of about 0.1% in the acidic solution 220 |
| Second-selecting step: selecting the food substance from the group consisting of water, a flavored drink, a juice, a dressing, a pudding, a yogurt, a gelatin, a frosting, and honey; and utilizing a targeted quantity of Trichuris suis ova in the acidic solution 225 |
| Third-limiting step: limiting the targeted quantity to number within a range of 250 to 2500 viable Trichuris suis ova per food product 230 |
| Second-forming step: forming an edible coating on a portion of the mixing solution, wherein the portion contains a number of Trichuris suis ova per unit of weight 235 |
| Third-selecting step: selecting the coating from the group consisting of chocolate, wax, and polymer 240 |
| Second-adding step: adding a flavoring to the consumable product 245 |
| Minimizing step: minimizing mechanical stirring when combining the mixing solution and the food substance 250 |
| Feeding step: feeding the consumable product to a human or a non-human animal 255 |
| Choosing step: choosing the food substance having a maximum pH of 5.0 260 |

FIG.2

METHOD OF MAKING A CONSUMABLE PRODUCT WITH PURIFIED EMBRYONATED *TRICHURIS SUIS* OVA

TECHNICAL FIELD

In the field of chemistry and molecular biology and microbiology, a process is disclosed for making a product containing a microorganism is synthesized.

BACKGROUND ART

Methods of producing and isolating parasite eggs for treating an autoimmune or allergic disease in a human or animal have been disclosed. These methods are important because observational studies on a number of immunologic diseases resulting from a dysregulated mucosal immune system may be corrected by treatment with embryonated *Trichuris suis* eggs (TSO). Reported are beneficial results for rheumatoid arthritis, multiple sclerosis, asthma, psoriasis, some IgE mediated food allergies (e.g. peanut allergy), and inflammatory bowel disease also known as ulcerative colitis and Crohn's Disease. These maladies have a much higher incidence in developed countries than in underdeveloped countries where helminths infections are common. Thus, it has been postulated that the increased frequency of these immunologic diseases in developed countries may be attributed to the reduced incidence of infections with intestinal helminths. Generally in clinical trials, patients ingested 2500 viable TSO every 2 or 3 weeks for at least 12 weeks.

Clinical studies have been reported using TSO for the treatment of inflammatory bowel disease (both Crohn's disease and ulcerative colitis) and positive results were reported.

In one such study, a randomized, double blind, placebo-controlled trial included 54 patients with active colitis, defined by an Ulcerative Colitis Disease Activity Index of >4. Patients were randomly assigned to receive placebo or TSO. Patients received 2500 *Trichuris suis* ova or placebo orally at 2-week intervals for 12 weeks. The primary efficacy variable was improvement of the Disease Activity Index to >4. After 12 weeks of therapy, improvement according to the intent-to-treat principle occurred in 13 of 30 patients (43.3%) with TSO treatment compared with 4 of 24 patients (16.7%) given placebo (P=0.04). Improvement was also found with the Simple Index that was significant by week 6. The difference in the proportion of patients who achieved an Ulcerative Colitis Disease Activity Index of 0-1 was not significant. Treatment reportedly induced no side effects.

In another example, a clinical study was performed on patients with active Crohn's disease to determine the safety and possible efficacy of treatment with intestinal TSO. In this study, twenty-nine patients with active Crohn's disease, defined by a Crohn's disease activity index (CDAI)>220 were enrolled. All patients ingested 2500 live TSO every three weeks for 24 weeks, and their disease activity was monitored by CDAI. Remission was defined as a decrease in CDAI to less than 150 while a response was defined as a decrease in CDAI of greater than 100. At week 24, 23 patients (79.3%) responded (decrease in CDAI, 100 points or CDAI, 150) and 21/29 (72.4%) remitted (CDAI, 150). Mean CDAI of responders decreased 177.1 points below baseline. Analysis at week 12 yielded similar results. There were no adverse events. These findings also support the premise that natural exposure to TSO affords protection from immunological diseases like Crohn's disease.

In another exemplary study that has been reported, the safety and effects of TSO was examined for patients with multiple sclerosis (MS), a phase 1 Helminth-induced Immunomodulatory Therapy (HINT 1). In this study, five patients with newly diagnosed, treatment-naive relapsing-remitting multiple sclerosis (RRMS) received 2500 TSO orally every 2 weeks for 3 months in a baseline versus treatment control exploratory trial. The mean number of new gadolinium-enhancing magnetic resonance imaging (MRI) lesions (n-Gd+) fell from 6.6 at baseline to 2.0 at the end of TSO administration, and 2 months after TSO was discontinued, the mean number of n-Gd+ rose to 5.8. No significant adverse effects were observed. In preliminary immunological investigations, increases in the serum level of the cytokines IL-4 and IL-10 were noted in four of the five subjects. TSO was well tolerated in RRMS, and favorable trends were observed in exploratory MRI and immunological assessments.

Helminths are worm-like animals (whip worms) that can live in the intestine or elsewhere in the body. Helminths have been reported to influence the host's mucosal immune response to limit inflammation and induce regulatory immune cells and immune regulatory pathways in the host. *Trichuris suis* is a natural parasite of pigs that hatch in the gastrointestinal tract in of swine and embed in the colonic wall. The worms were gradually expelled from week 5 to 11. While embedded in the colonic wall of pigs the *Trichuris suis* expel eggs in the feces.

In humans, embryonated *Trichuris suis* ova (TSO) hatch in the gastrointestinal tract and the larvae colonize the colonic wall briefly, but do not establish an infection [Summers, et al. (2005b)]. After a single treatment with 2500 infective eggs a transitory upregulated Th2-response (e.g. IL-4, IL-5, IL-13) was measurable at 3 weeks in the ileocaecal lymph nodes, while a more prolonged Th2-response was found in the colon mucosa. However, unlike the pig, the *Trichuris suis* worms cannot access the bloodstream from the crypts during colonization of the human gastrointestinal tract, thus they are unable to mature. They die within 2-3 weeks and are fully digested without producing eggs. Therefore, there is no expansion of the infection in humans and there also is no danger infecting others.

Methods for the recovery of eggs from the intestines or feces of pigs have been developed. The finished embryonated TSO product is stored at room temperature in a storage solution containing standard food preservatives. The TSO can be frozen and remain viable upon thawing. Although there has been no systematic testing of the effect of desiccation upon TSO, in nature, the eggs are shed into the soil where they may be desiccated, but remain viable for as many as nine years.

Methods are known and available for the isolation of TSO using dilute sulfuric acid from either porcine intestines or fecal material as the starting material. In these methods, embryonation is accomplished using a dilute solution of sulfuric acid having a pH below 6.

*Trichuris suis* ova (TSO), have been tested for viability using in vitro and in vivo methods. The influence of pH, different chemical, physical, and biological factors have been investigated for effects on TSO hatching.

The metabolism of TSO is greatly reduced by freezing or desiccation. However, incubation of eggs with mucosal scrapings from the ileum, caecum, and colon for 24 hours at 38° C. significantly increased hatching. It has also been reported that *Ascaris lumbricoides* ova are destroyed quickly at temperatures above 51° C., but are unaffected by long exposures to temperatures 47° C. or less.

SUMMARY OF INVENTION

A method of making a consumable product containing purified embryonated *Trichuris suis* ova (TSO) preferably includes steps of: storing the TSO in an acidic solution; adding a food preservative to the acidic solution to produce a preservative-acid-solution; forming a mixing solution by raising the pH of the preservative-acidic-solution to match the pH of a food substance by titrating the preservative-acidic-solution with an acid neutralizer so that the pH changes at a rate of not more than 1 pH unit per 24 hours; and producing the consumable product by combining the mixing solution and the food substance while maintaining the temperature of the consumable product between 1 degree Centigrade and 47 degrees Centigrade.

Optional steps include making the acidic solution from at least one of vinegar, phosphoric acid, acetic acid, and citric acid; selecting the food preservative from at least one of sodium citrate, sodium sorbate, and sodium benzoate; limiting the sodium sorbate to a concentration of less than 0.3% sorbate in the acid solution; limiting the sodium benzoate to a concentration of about 0.1% in the acidic solution; selecting the food substance from the group consisting of water, a flavored drink, a juice, a dressing, a pudding, a yogurt, a gelatin, a frosting, and honey while utilizing a targeted quantity of *Trichuris suis* ova in the acidic solution; limiting the targeted quantity to number within a range of 250 to 2500 viable *Trichuris suis* ova per food product; forming an edible coating on a portion of the mixing solution, wherein the portion contains a number of *Trichuris suis* ova per unit of weight; selecting the coating from at least one of chocolate, wax, and polymer; adding a flavoring to the consumable product; minimizing mechanical stirring when combining the mixing solution and the food substance; and using the consumable product by feeding it to a human or a non-human animal.

Technical Problem

The early positive results in clinical trials indicate a need for further study of administering TSO to humans and animals with autoimmune or allergic disease. In this regard, there is a need for easy and effective means for administering TSO in a food product that can be consumed by humans and animals.

It is known that embryonated TSO can undergo breakdown or may start hatching. Previously, when helminths ova were treated with either acid or base, experimenters experienced this hatching pattern (hatching started at day 1 and finished by day 5). Mechanical stimulation of the TSO also initiates hatching, such as stimulation when glass beads were utilized in a simple and reproducible method for egg hatching. Finally, experimenters showed that bacterial growth involving all strains of *Escherichia coli* tested initiated hatching of helminths ova.

A method is needed for making a food product for consumption by humans and non-human animals that contains viable, purified embryonated *Trichuris suis* ova and that minimizes bacterial growth, TSO breakdown, and hatching of the TSO.

Solution to Problem

The solution to the problem of a lack of a stable and suitable food product containing purified embryonated *Trichuris suis* ova (TSO) is the method of producing the food product according to the steps disclosed herein.

In the preparation of a food product containing TSO, breakdown and hatching of the eggs is a problem that addressed in the method by very slowly adjusting the pH of the acidic suspension containing the TSO. The present invention minimizes breakdown and hatching of the TSO by limiting changes in pH of an acidic solution containing TSO to no more than about 1 unit per 24 hours and preferably to pH 5.0 or lower.

In addition, in order to avoid hatching and reducing the viability of the eggs, the initial TSO and the production and storage of the food product containing eggs is performed at temperatures between approximately 1° C. and 47° C.

In addition, in order to avoid premature hatching of the eggs, the process minimizes mechanical stimulation of the TSO when mixing to make the food product.

Thus, the solution utilizes purified embryonated TSO that are stored suspended in an acidic solution, such as for example vinegar (4% acetic acid) with any standard food preservative, such as those that are generally recognized as safe: those typically include sodium citrate, sodium sorbate (<0.3% sorbate) and/or sodium benzoate 0.1%. If the acidic solution is to be mixed into a food product, the pH of the acidic solution is slowly titrated (no more than 1 pH unit per 24 hours) to the pH of food product (preferably having a pH of 5.0 or lower) that the TSO is to be mixed with. Mixing is accomplished with minimal mechanical disruption maintaining the temperature of the solution and food product between 1° C. and 47° C. A pH adjusted suspension of viable TSO may be encapsulated with chocolate, wax, or edible polymer coated and added to dry food product. TSO is preferably added at a standard unit dose, such as for example, 250 or 2500 viable TSO per food product consumed in one sitting, i.e., bottle of juice or water.

Advantageous Effects of Invention

The method produces a food product that facilitates the administration of TSO in clinical studies and other testing of treatment for immunologic diseases thought to result from a dysregulated mucosal immune system.

BRIEF DESCRIPTION OF DRAWINGS

The drawings illustrate preferred and optional steps in the method of making a consumable product with purified embryonated *Trichuris suis* ova according to the disclosure. The reference numbers in the drawings are used consistently throughout. Reference numbers in FIG. 1 are given 100 series numbers. Similarly, new reference numbers in FIG. 2 are given the 200 series numbers.

FIG. 1 is a flow chart of the steps of a preferred embodiment of the method of making the consumable product with purified embryonated *Trichuris suis* ova.

FIG. 2 is a chart showing optional steps in alternative embodiments.

DESCRIPTION OF EMBODIMENTS

In the following description, reference is made to the accompanying drawings, which form a part hereof and which illustrate several embodiments of the present invention. The drawings and the preferred embodiments of the invention are presented with the understanding that the present invention is susceptible of embodiments in many different step combinations and, therefore, other embodiments may be utilized and operational changes may be made, without departing from the scope of the present invention.

Reference is made to FIG. 1 showing steps in a preferred embodiment of the method of making a consumable product with purified embryonated *Trichuris suis* ova (TSO). The consumable product, is also referred to as a food product, and it includes any substance consumed by a human, including as typical examples water, flavored drinks, juices, dressings, puddings, yogurt, gelatin, frostings, honey and dietary supplements.

This preferred embodiment is method of making (100) a consumable product, the consumable product comprising a purified embryonated *Trichuris suis* ova. The method includes a storing step (105); a first-adding step (110); a first-forming step (115); and a producing step (120).

The storing step (105) includes storing a purified embryonated *Trichuris suis* ova in an acidic solution. A preferable acidic solution uses vinegar with a 4% acetic acid. Vinegar is a liquid consisting mainly of acetic acid ($CH_3COOH$) and water. Acetic acid is usually produced by the fermentation of ethanol by acetic acid bacteria. Vinegar is preferred because it is itself a food product and it comprises a mild acid that is less likely to damage the TSO.

The first-adding step (110) includes adding a food preservative to the acidic solution to produce a preservative-acid-solution. Exemplary food preservatives include sodium citrate, sodium sorbate, and sodium benzoate, calcium propionate, sodium nitrate, sodium nitrite, disodium EDTA, and sulfites such as sulfur dioxide, sodium bisulfite, and potassium hydrogen sulfite.

The food preservative lengthens the shelf life of the consumable product, preferably so that if stored at a temperature within a specified temperature range of 1° C. to 47° C., the consumable product can be utilized throughout the testing period. The food preservative is also a widely used consumable product and so it is not something that will contaminate the consumable product resulting from the disclosed method.

The first-forming step (115) includes forming a mixing solution by raising the pH of the preservative-acidic-solution to match the pH of a food substance by titrating the preservative-acidic-solution with an acid neutralizer so that the pH changes at a rate of not more than 1 pH unit per 24 hours, optionally for a food substance having a maximum pH of 5.0. Thus, the first-forming step (115) may be accomplished with the choosing step (260) of choosing the food substance having a maximum pH of 5.0.

The pH number is a figure expressing the acidity or alkalinity of a solution on a logarithmic scale on which a number between 0 and 14 indicates if a chemical is an acid or a base. On this scale, a pH of less than 7 represents acidity, a pH of 7 indicates neutrality, and a pH of more than 7 represents alkalinity. Thus, a pH of 7 represents a neutral solution, lower values are more acid, and higher values more alkaline. The pH is the negative of the logarithm to base 10 of the concentration of hydrogen ions in moles per liter. The pH may be mathematically shown as equal to $-\log_{10} c$, where c is the hydrogen ion concentration in moles per liter.

The producing step (120) includes producing the consumable product by combining the mixing solution and the food substance, said producing performed while maintaining the temperature of the consumable product between 1 degree Centigrade and 47 degrees Centigrade.

FIG. 2 illustrates optional steps in the method. The dotted line connecting the boxes showing the steps is intended to signify that each of the steps is optional. The optional steps include a making step (205); a first-selecting step (210); a first-limitation step (215); a second-limitation step (220); a second-selecting step (225); a third-limiting step (230); a second-forming step (235); a third-selecting step (240); a second-adding step (245); a minimizing step (250); and a feeding step (255).

The making step (205) includes of making the acidic solution using a formulation selected from the group consisting of vinegar, phosphoric acid, acetic acid, and citric acid. These acids are commonly found in food products. Phosphoric acid is commonly found in soft drinks to provide a sharper, tangy taste and to help slow the growth of molds and bacteria in sugary formulas. Acetic acid is the main component of vinegar and is thus a consumable food. Citric acid is a weak organic tribasic acid: It occurs naturally in citrus fruits. Use of an acid that is commonly consumed in foods is preferred for the making step (205).

The first-selecting step (210) includes of selecting the food preservative from at least one of sodium citrate, sodium sorbate, and sodium benzoate.

The first-limitation step (215) includes of limiting the sodium sorbate to a concentration of less than 0.3% sorbate in the acid solution.

The second-limitation step (220) includes of limiting the sodium benzoate to a concentration of about 0.1% in the acidic solution.

The second-selecting step (225) includes of selecting the food substance from the group consisting of water, a flavored drink, a juice, a dressing, a pudding, a yogurt, a gelatin, a frosting, and honey; and utilizing a targeted quantity of *Trichuris suis* ova in the acidic solution. Use of a liquid or soft food substance makes it easier to combine the mixing solution containing the TSO with the food substance while minimizing mechanical disruption of the combination.

The third-limiting step (230) includes of limiting the targeted quantity to number within a range of 250 to 2500 viable *Trichuris suis* ova per food product. This covers the range of egg content that is used in the clinical trials and testing.

The second-forming step (235) includes of forming an edible coating on a portion of the mixing solution, wherein the portion contains a number of *Trichuris suis* ova per unit of weight. An edible coating can make administering the food product much more pleasing to the test subject.

The third-selecting step (240) includes of selecting the coating from the group consisting of chocolate, wax, and polymer.

The second-adding step (245) includes of adding a flavoring to the consumable product. A flavoring can make the food product enjoyable to consume.

The minimizing step (250) includes of minimizing mechanical stirring when combining the mixing solution and the food substance.

The feeding step (255) includes of feeding the consumable product to a human or a non-human animal. Thus the feeding step (255) is a method of using the consumable product.

The above-described embodiments including the drawings are examples of the invention and merely provide illustrations of the invention. Other embodiments will be obvious to those skilled in the art. Thus, the scope of the invention is determined by the appended claims and their legal equivalents rather than by the examples given.

INDUSTRIAL APPLICABILITY

The invention has application to the human and animal health food and pharmaceutical industries.

What is claimed is:

1. A method of making a consumable product, the consumable product comprising a purified embryonated *Trichuris suis* ova, the method comprising the steps of:
    storing a purified embryonated *Trichuris suis* ova in an acidic solution;
    adding a food preservative to the acidic solution to produce a preservative-acid-solution;
    selecting a food substance with a pH number greater than the pH of the preservative acid solution;
    forming a mixing solution by raising the pH of the preservative-acidic-solution to match the pH of the food substance by titrating the preservative-acidic-solution with an acid neutralizer so that the pH changes at a rate of not more than 1 pH unit per 24 hours; and
    producing the consumable product by combining the mixing solution and the food substance, said producing performed while maintaining the temperature of the consumable product between 1 degree Centigrade and 47 degrees Centigrade.

2. The method of claim 1, further comprising the step of making the acidic solution using a formulation selected from the group consisting of vinegar, phosphoric acid, acetic acid, and citric acid.

3. The method of claim 1, further comprising the step of selecting the food preservative from at least one of sodium citrate, sodium sorbate, and sodium benzoate.

4. The method of claim 3, further comprising the step of limiting the sodium sorbate to a concentration of less than 0.3% sorbate in the acid solution.

5. The method of claim 3, further comprising the step of limiting the sodium benzoate to a concentration of about 0.1% in the acidic solution.

6. The method of claim 1, further comprising the step of choosing the food substance having a maximum pH of 5.0.

7. The method of claim 1, further comprising the steps of:
    selecting the food substance from the group consisting of water, a flavored drink, a juice, a dressing, a pudding, a yogurt, a gelatin, a frosting, and honey; and
    utilizing a targeted quantity of *Trichuris suis* ova in the acidic solution.

8. The method of claim 7, further comprising the step of limiting the targeted quantity to number within a range of 250 to 2500 viable *Trichuris suis* ova per food product.

9. The method of claim 1, further comprising the step of forming an edible coating on a portion of the mixing solution, wherein the portion contains a number of *Trichuris suis* ova per unit of weight.

10. The method of claim 9, further comprising the step of selecting the coating from the group consisting of chocolate, wax, and polymer.

11. The method of claim 1, further comprising the step of adding a flavoring to the consumable product.

12. The method of claim 1, further comprising the step of minimizing mechanical stirring when combining the mixing solution and the food substance.

13. A method of using the consumable product made by the method of claim 1, the method comprising the step of feeding the consumable product to a human or a non-human animal.

* * * * *